United States Patent
Meyer

(10) Patent No.: US 10,436,733 B2
(45) Date of Patent: Oct. 8, 2019

(54) METHOD OF MEASURING CAPACITANCE OF ROW AND COLUMN ELECTRODES OF CAPACITIVE IMAGING DEVICE

(71) Applicant: Advanced Sensor Technology Limited, Road Town, Tortola (VG)

(72) Inventor: Hans Ulrich Meyer, Morges (CH)

(73) Assignee: HEMY8 SA, Morges (CH)

( * ) Notice: Subject to any disclaimer, the term of this patent is extended or adjusted under 35 U.S.C. 154(b) by 23 days.

(21) Appl. No.: 15/455,378

(22) Filed: Mar. 10, 2017

(65) Prior Publication Data

US 2017/0261459 A1   Sep. 14, 2017

Related U.S. Application Data

(60) Provisional application No. 62/306,792, filed on Mar. 11, 2016.

(51) Int. Cl.

| | |
|---|---|
| *G01R 27/26* | (2006.01) |
| *G01N 27/22* | (2006.01) |
| *G06F 3/044* | (2006.01) |
| *G06F 3/041* | (2006.01) |
| *G06K 9/00* | (2006.01) |
| *G06F 3/0354* | (2013.01) |

(52) U.S. Cl.
CPC ....... *G01N 27/226* (2013.01); *G01R 27/2605* (2013.01); *G06F 3/03547* (2013.01); *G06F 3/044* (2013.01); *G06F 3/0416* (2013.01); *G06K 9/0002* (2013.01); *G06F 2203/04104* (2013.01); *G06F 2203/04107* (2013.01); *G06F 2203/04111* (2013.01)

(58) Field of Classification Search
CPC .. G01R 27/2605; G01N 27/226; G06F 3/044; G06F 3/03547; G06F 3/0416; G06K 9/0002
USPC .................................................. 324/658–690
See application file for complete search history.

(56) References Cited

U.S. PATENT DOCUMENTS

| | | | |
|---|---|---|---|
| 7,663,607 B2 | 2/2010 | Hotelling et al. | |
| 8,476,912 B2 | 7/2013 | Dorrough | |
| 8,654,098 B2 | 2/2014 | Ningrat | |
| 8,773,146 B1 * | 7/2014 | Hills | G01N 27/22 324/658 |
| 9,103,929 B2 | 8/2015 | Krapf et al. | |
| 2006/0064612 A1 * | 3/2006 | Knapp | G09G 3/20 714/724 |
| 2010/0252335 A1 * | 10/2010 | Orsley | G06F 3/044 178/18.03 |

(Continued)

*Primary Examiner* — Patrick Assouad
*Assistant Examiner* — Demetrius R Pretlow
(74) *Attorney, Agent, or Firm* — Leydig, Voit & Mayer

(57) ABSTRACT

A capacitive imaging method or device using an array of row electrodes 101 and column electrodes 102 on a substrate 100, wherein cross-capacitance between row and column electrodes is obtained from row electrode 101 self-capacitance measured with the remaining electrodes grounded, column electrode 102 self-capacitance measured with the remaining electrodes grounded, and combined row and column electrode self-capacitance measured with the remaining electrodes grounded. A preferred embodiment is a hand-held wall scanner for detecting hidden features having a two-dimensional display the size of the array and located over it. Hidden features influencing row-to-column cross-capacitances are thus imaged in real size and at their real location.

5 Claims, 5 Drawing Sheets

(56) References Cited

U.S. PATENT DOCUMENTS

| | | | | |
|---|---|---|---|---|
| 2011/0261006 | A1* | 10/2011 | Joharapurkar | G06F 3/0416 345/174 |
| 2012/0113071 | A1* | 5/2012 | Kawaguchi | G06F 3/044 345/204 |
| 2013/0069905 | A1* | 3/2013 | Krah | G06F 3/044 345/174 |
| 2013/0229382 | A1* | 9/2013 | Huang | G06F 3/044 345/174 |
| 2013/0257767 | A1* | 10/2013 | Wu | G06F 3/044 345/173 |
| 2013/0285972 | A1* | 10/2013 | Elias | G06F 3/044 345/174 |
| 2014/0002406 | A1* | 1/2014 | Cormier, Jr. | G06F 3/044 345/174 |
| 2014/0368460 | A1* | 12/2014 | Mo | G06F 3/0416 345/174 |
| 2015/0242043 | A1* | 8/2015 | Oda | G06F 3/044 345/174 |
| 2015/0277624 | A1* | 10/2015 | Yeh | G06F 3/044 345/174 |
| 2015/0331535 | A1* | 11/2015 | Li | G06F 3/044 348/174 |
| 2016/0103550 | A1* | 4/2016 | Snelgrove | G06F 3/0416 345/174 |
| 2016/0154507 | A1* | 6/2016 | Bharathan | G06F 3/011 345/174 |
| 2016/0224171 | A1* | 8/2016 | Kim | G06F 3/0488 |
| 2016/0259474 | A1* | 9/2016 | King | G06F 3/0416 |

* cited by examiner

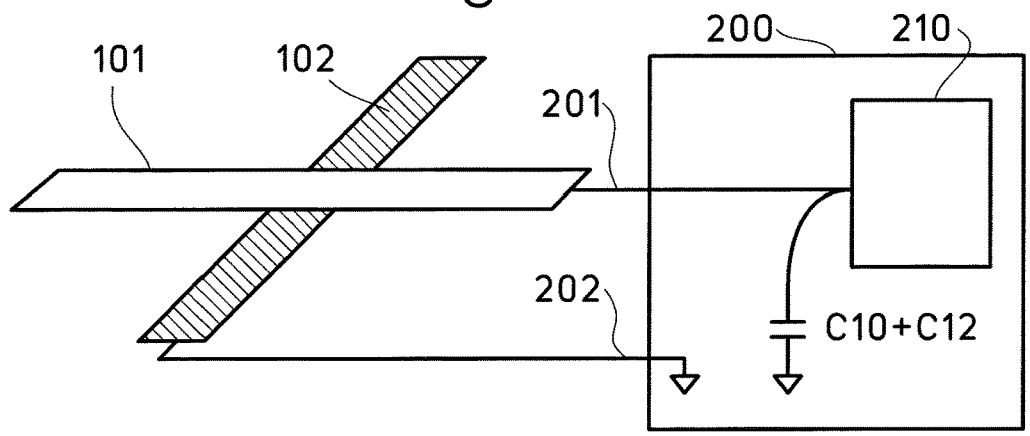
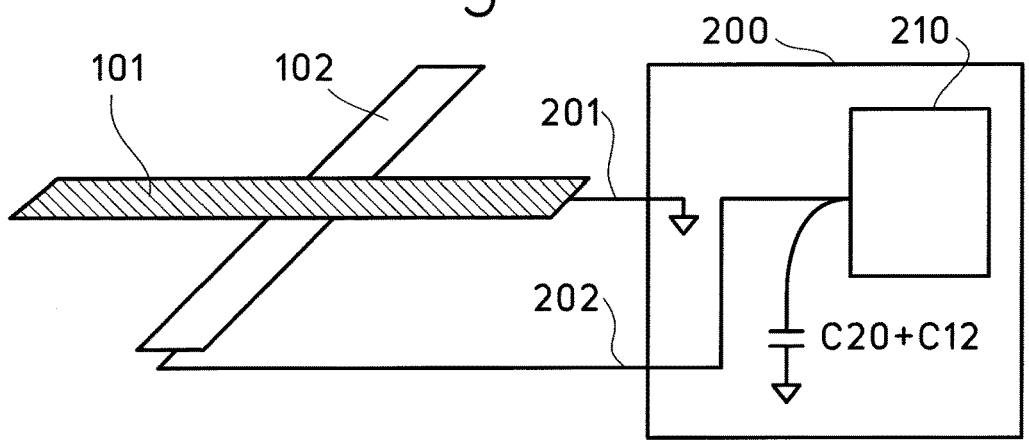
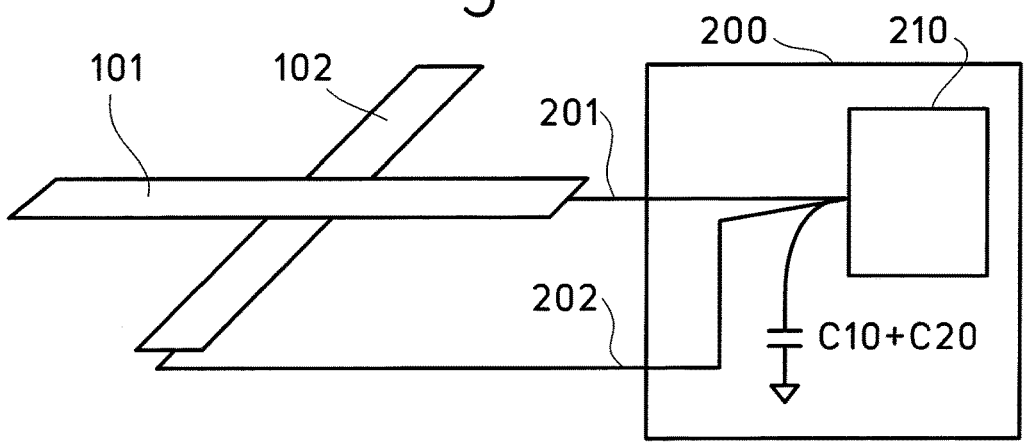

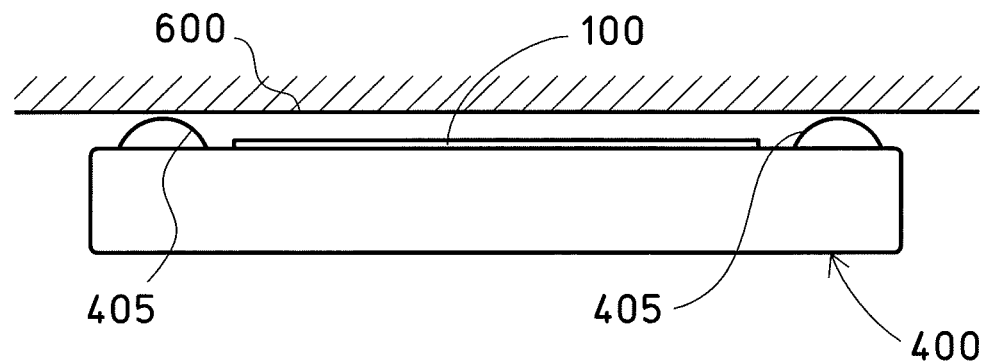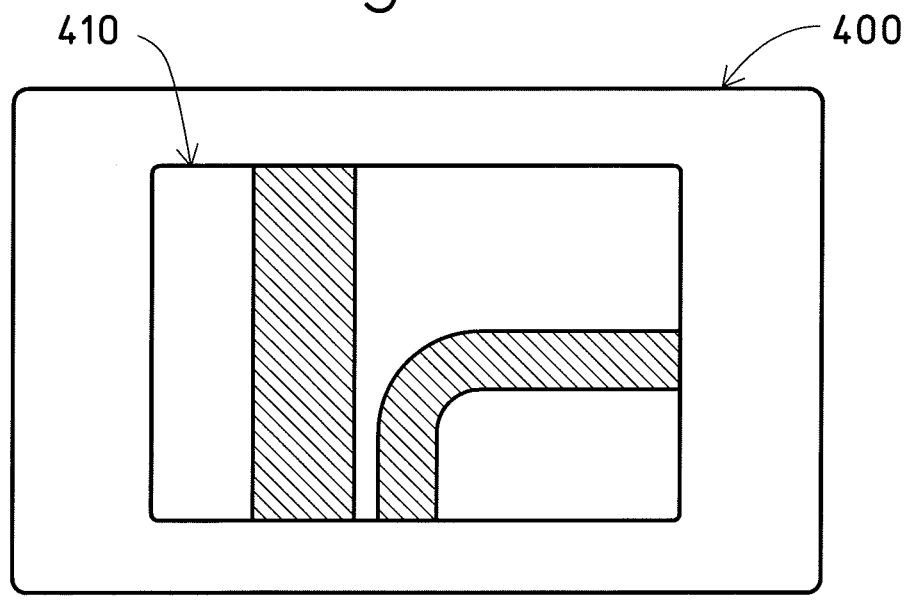

METHOD OF MEASURING CAPACITANCE OF ROW AND COLUMN ELECTRODES OF CAPACITIVE IMAGING DEVICE

FIELD OF THE INVENTION

The invention relates to a capacitive imaging device and method using an array of row and column electrodes to locate features nearby, such as fingers on a track pad or multi-touch screen embodiment, or studs, pipes and wiring in a hidden object detector or stud finder.

BACKGROUND OF THE INVENTION

Capacitive imaging devices using an array of M row electrodes and N column electrodes are competing with devices using a grid of M by N electrodes connected to a processing circuit through M times N connecting lines, or through a minimum of M times N active elements such as field effect transistors. An array of M row and N column electrodes, though, can be implemented on any substrate and only requires M plus N connections for sensing the M times N row-to-column mutual or cross-capacitances concentrated near row-to-column crossovers.

State-of-the-art capacitive imaging devices using an array of row and column electrodes sense cross-capacitances by one electrode set (rows or columns) operating as drivers coupling to the other electrode set operating as pickups, as disclosed in U.S. Pat. No. 7,663,607 (Hotelling et al.), specifically in FIG. 9 and related text. To keep the measurement unaffected by pickup electrode capacitive loading, a charge amplifier (an operational amplifier with capacitive feedback from output to inverting input) can be inserted, as disclosed in FIG. 13 and related text.

However, cross-capacitance coupling from a drive electrode to a pickup electrode only takes place near their crossover, while interfering signals from voltage sources such as AC lines may couple to a substantial part of the pickup line, adding noise to the measurements.

As disclosed in an embodiment of U.S. Pat. No. 8,654,098 (Ningrat) a measurement of the column electrodes' self-capacitance is combined with the aforementioned row-to-column cross-capacitance measurement, and both data sets combined to reduce the effect of noise. This more complex approach only works for touch detection, though.

For hidden object detectors, the capacitive image is best displayed to the user by a display right over or near the capacitive electrode array. The two next patents are only mentioned here for their capacitive image display, neither of them disclosing row and column electrodes. U.S. Pat. No. 8,476,912 (Dorrough) discloses a stud sensor having a linear array of electrodes covered by a linear array of LEDs, letting the user "see" the studs along the line. U.S. Pat. No. 9,103,929 (Krapf et al.) discloses a planar array of individually addressable electrodes or pixels, covered by a planar array of display points, letting the user "see" the hidden objects. Imaging and display arrays of similar size create the illusion of a "window" through which hidden objects can be "seen", helping users to identify hidden objects.

SUMMARY OF THE INVENTION

It is an object of the invention to overcome shortcomings in prior art capacitive imaging devices and methods using an array of row and column electrodes.

Accordingly, there is provided a capacitive imaging device and method using an array of row electrodes and column electrodes, wherein cross-capacitance between rows and columns is obtained from row electrode self-capacitance, from column electrode self-capacitance, and from combined row and column electrode self-capacitance.

In an embodiment of the invention, cross-capacitance between a row electrode and a column electrode is obtained from the row electrode's self-capacitance measured with the remaining electrodes grounded, from the column electrode's self-capacitance measured with the remaining electrodes grounded, and from the combined row electrode's and column electrode's self-capacitance measured with the row electrode and column electrode connected together and the remaining electrodes grounded.

In an embodiment of the invention, cross-capacitance between multiple row electrodes and multiple column electrodes is obtained from the multiple row electrodes' self-capacitance measured with the multiple row electrodes connected together and the remaining electrodes grounded, from the multiple column electrodes' self-capacitance measured with the multiple column electrodes connected together and the remaining electrodes grounded, and from the combined self-capacitance measured with the multiple row electrodes and the multiple column electrodes connected together and the remaining electrodes grounded.

Preferably, row-to-column cross-capacitance is obtained by adding the row electrode self-capacitance to the column electrode self-capacitance and subtracting the combined row and column electrode self-capacitance.

Advantageously, the cross-capacitances obtained after power-on or at any other convenient time can be mapped in memory to be subtracted as an offset from cross-capacitance values obtained later.

Preferably, measurements of row electrode self-capacitance, combined row and column self-capacitance, and column self-capacitance follow each other in quick succession.

Optionally, rows and columns are shaped to be narrower near their crossovers and wider in-between.

Advantageously, a screen shields the electrodes on the side facing away from the objects to be detected.

Favorably, the screen is formed on the side of a substrate facing the electrode array, with the circuitry implemented on the side looking away from the electrode array.

The electronic circuit is at least partially implemented on the same substrate as the electrode array.

The screen may be integrated as a conducting layer on the same substrate as the electrode array.

A preferred embodiment of the invention is a hidden object detector.

Advantageously, the display used for the hidden object detector has approximately the same size than its capacitive imaging device and covers it.

Advantageously, the capacitive imaging device is enabled to transmit data to a device such as a smart phone, a tablet or a laptop.

BRIEF DESCRIPTION OF THE DRAWING

FIGS. 2A, 2B, and 2C show, in principle, the three self-capacitance measurements done for a row/column electrode combination in a capacitive imaging device and method according to the invention.

FIGS. 6A and 6B are top and elevation views of a preferred embodiment of the invention.

DESCRIPTION OF THE INVENTION

Electrical characteristics of capacitive imaging devices using an array of row and column electrodes are presented here to facilitate the description of the invention.

Figure 1A:
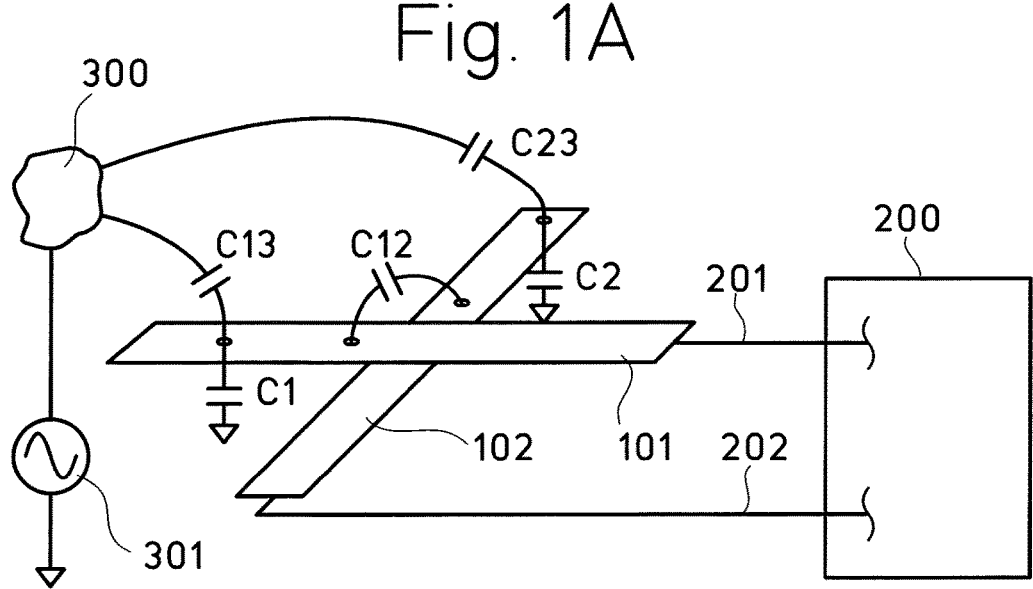
FIGS. 1A and 1B tutorially show equivalent lumped capacitance models in capacitive imaging devices using row and column electrodes.
Figure 1B:
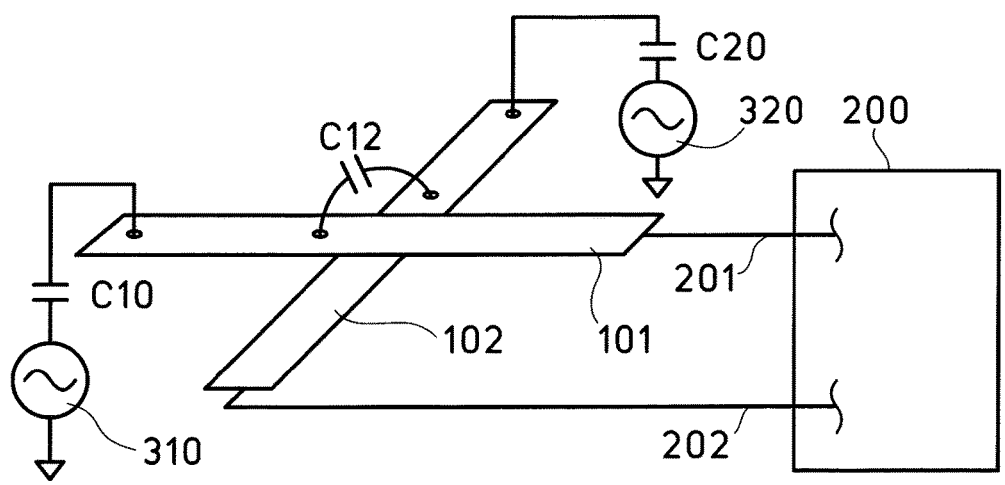

FIGS. 1A and 1B tutorially show, for a capacitive imaging device according to the invention, two equivalent lumped capacitance models of a row electrode 101 and a column electrode 102 including their connecting lines 201 and 202 to a measuring circuit 200, with the remaining row and column electrodes (not shown) grounded, that is, connected to ground or to a common potential.

Cross-capacitance C12 between row electrode 101 and column electrode 102, subject to the dielectric configuration in the vicinity of the row-to-column crossover, is the mutual capacitance of interest. Note that connecting lines 201, 202 and measuring circuit 200 also contribute to cross-capacitance C12. This concern will be addressed later.

In FIG. 1A self-capacitance C1 from row electrode 101 to ground also includes the capacitance of line 201 to ground, and self-capacitance C2 from column electrode 102 to ground, also includes the capacitance of line 202 to ground. There are finally mutual capacitances C13, from row electrode 101 to an external electrode 300 connected to a noise voltage source 301, and C23, from column electrode 102 to external electrode 300.

As quasi-static conditions prevail (shortest wavelength of interest much larger than device size), row electrode's 101 capacitances C1 to ground and C13 to noise voltage source 300 are electrically equivalent to a single capacitance C10=C1+C13 (C10 shown in FIG. 1B) coupled to a noise voltage source 310, and column electrode's 102 capacitances C2 and C23 are electrically equivalent to a single capacitance C20=C2+C23 (C20 shown in FIG. 1B) coupled to a noise voltage source 320. Capacitances C1, C2 to ground and C13, C23 to the noise voltage are thus replaced by C10, C20, shown in FIG. 1B, coupled to noise voltage sources 310, 320.

For simplification, C10 and C20 are tied to ground in FIGS. 2A to 2C showing the principle of the invention in the absence of noise. This simplification will of course be avoided when analyzing the effect of noise.

Returning to FIG. 1B, the influence of capacitances C10 and C20 should be eliminated in the measurement of cross-capacitance C12. In prior art a drive signal on a column or row couples through cross-capacitance C12 and is sensed by the corresponding row or column, loaded by capacitance C10 or C20.

According to the invention, row and column electrodes' cross-capacitance can be obtained by measuring three self-capacitances with a microcontroller including a self-capacitance-to-digital converter. FIGS. 2A to 2C show the principle of obtaining the cross-capacitance C12 of a row electrode 101 and a column electrode 102. The self-capacitance measurements are done on row electrode 101 and column electrode 102 with the remaining electrodes (not shown) grounded. Row electrode 101 and column electrode 102 are respectively connected by lines 201 and 202 to measuring circuit 200, which can switch each line 201 and 202 either to ground (or common potential), or to the self-capacitance-to-digital converter 210 (switches are not shown in FIGS. 2A to 2C).

FIG. 2A shows the measurement of the self-capacitance of row electrode 101 with column electrode 102 grounded. In measuring circuit 200, line 201, hence row electrode 101, is switched to self-capacitance-to-digital converter 210, and line 202, hence column electrode 102, is switched to ground: the self-capacitance-to-digital converter senses capacitance C10 of row electrode 101, plus cross-capacitance C12 to grounded column electrode 102, bringing the sensed self-capacitance to C10+C12.

FIG. 2B shows the measurement of the self-capacitance of column electrode 102 with row electrode 101 grounded. In measuring circuit 200, line 202, hence column electrode 102, is switched to self-capacitance-to-digital converter 210, and line 201, hence row electrode 101, is switched to ground. The self-capacitance-to-digital converter thus senses capacitance C20 of column electrode 102, plus cross-capacitance C12 to grounded row electrode 101, bringing the sensed self-capacitance to C20+C12.

FIG. 2C shows the measurement of the self-capacitance of row electrode 101 and column electrode 102 connected together. In measuring circuit 200, line 201, hence row electrode 101, and line 202, hence column electrode 102, are switched together to self-capacitance-to-digital converter 210. Self-capacitance-to-digital converter 200 thus senses both capacitances C10 and C21, but not cross-capacitance C12, whose terminals are at the same voltage, so that the sensed self-capacitance is just C10+C20.

Adding the two former self-capacitances and subtracting the latter, one gets:

$$(C10+C12)+(C20+C12)-(C10+C20)=2\ C12.$$

Only cross-capacitance C12 remains in the result, as capacitances C10 and C20 of row and column electrodes 101 and 102 (including lines 201 and 202) cancel out and do not matter anymore, provided their sum remains within the converter's input range. This makes the layout of row and column electrodes and their connecting lines easier, as it is only necessary to shield row electrode connecting lines 201 from column electrode connecting lines 202, or at least keep them apart, so as to minimize the contribution of parasitic cross-capacitance from outside the array of row and column electrodes to cross-capacitance C12.

An advantage of the method according to the invention is that the required circuitry can be implemented with a low-cost microcontrollers like Silicon Labs' microcontroller family C8051F97x, incorporating fast and accurate self-capacitance-to-digital converters whose input can be switched to one or several of the microcontroller's sensing pads, with the unselected sensing pads grounded.

Figure 3:
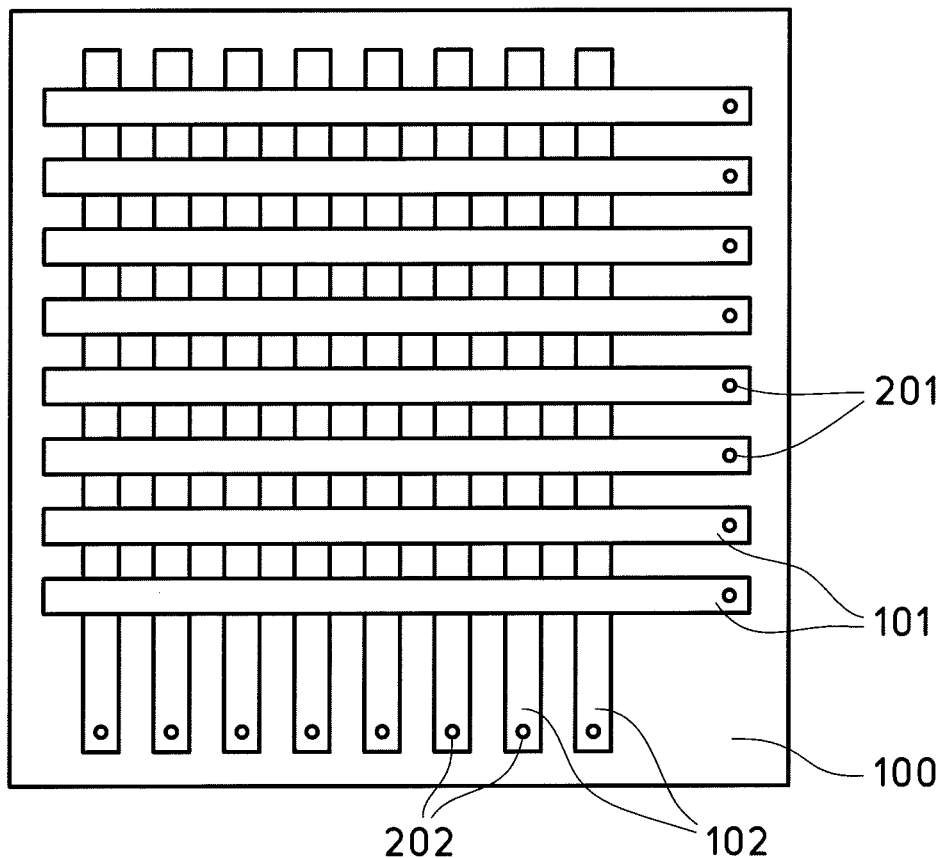
FIG. 3 shows an array of row and column electrodes on a substrate, with row electrodes on one side of the substrate and column electrodes on the other.

The range or distance from the array at which dielectric or conducting objects can be sensed is of the order of a row's or column's pitch. The electrodes 101 and 102 on either side of substrate 100, shown in transparence in FIG. 3, are usually straight for tolerance to both sides' misalignment, but as known from prior art, range can be improved by narrowing the electrodes near crossovers and widening them in-between; this will be commented further below.

Another way to increase the detecting range without a significant decrease in resolution is to connect row electrodes together and column electrodes together to form electrically wider rows and columns, for example rows one and two connected together and then rows two and three connected together. The shift from one such combined row to the next, is the same as for single row electrodes, so that resolution is only marginally affected. This scheme is not limited to adjacent rows: the first and third row could be connected together and the second row left out (switched to ground), and then the second and fourth rows could be connected together and the third row left out, and so on.

The measurement method according to the invention shown in FIGS. 2A to 2C for single row electrodes and single column electrodes also applies to multiple row electrodes and multiple column electrodes, with multiple row electrodes replacing single row electrodes and multiple column electrodes replacing single column electrodes. Specifically, the following self-capacitances are measured: the self-capacitance of the multiple row electrodes switched to the self-capacitance-to-digital converter with the remaining electrodes grounded, the self-capacitance of the multiple column electrodes switched to the self-capacitance-to-digital converter with the remaining electrodes grounded, and the self-capacitance of all combinations of a multiple row electrode and a multiple column electrode switched together to the self-capacitance-to-digital converter, with the remaining electrodes grounded.

Measuring either with single electrodes or with electrodes formed by multiple interconnected electrodes in a same embodiment adds the choice of detecting fine dielectric features or inhomogeneities at close range with single electrodes, or also more distant but larger features with multiple electrodes, allowing for more in-depth perception.

As all capacitances other than cross-capacitance C12 cancel out, imaging accuracy and stability are maximized. Still, as already remarked, cross-capacitances C12 are not limited to the electrodes' crossover zones, as connecting lines 201, 202 and measuring circuit 200 also contribute to them. Layout and shielding may reduce their contribution but not eliminate it. The influence of objects, especially remote ones, on cross-capacitance being quite small, it may become necessary to compensate the contribution to cross-capacitance C12 from connecting lines 201, 202 and from measuring circuit 200.

This can be done by a calibration during which cross-capacitances are obtained in the absence of objects near the row and column electrodes, and mapped in memory as offsets. After calibration, each cross-capacitance obtained is corrected by the stored offset previously obtained at the same location, so that just after calibration all corrected cross-capacitances remain around zero until a dielectric feature appears nearby. If these parasitic cross-capacitances remain constant, the calibration needs to be done only once at the factory. If they drift with time, calibration can be done at every power-on.

In many embodiments of the invention, coupling from noise voltage sources is a major concern, especially from 50/60 Hz power lines, either directly, as in hidden object detectors, or indirectly, through other conducting bodies or extremities, like an electrically ungrounded person's fingers on a touch detector or trackpad; or of an ungrounded person holding the device. Looking back at FIG. 1B, it is clear that equivalent row and column noise voltage sources 310 and 320 couple through capacitances C10 and C20 much larger than cross-capacitance C12 of which, moreover, only a fraction is affected by objects nearby.

However, if the three self-capacitance measurements shown in FIGS. 2A to 2C follow each other with only a small delay, the noise's lower-frequency components will not vary much from one measurement to the next: the capacitances C10 and C20 being the same and the noise voltage source or at least its low frequency components around 50/60 Hz being almost the same, the subtraction of two measurements in quick succession will reject the noise. For this, the self-capacitance-to-digital converter must be fast enough: in the Silicon Labs microcontrollers cited, the minimum conversion time, which dictates the delay between samples, is of the order of 30 microseconds. The inverse (tau) of the circular frequency (omega) of a 50/60 Hz voltage source being around 3 milliseconds means that successive noise voltage samples vary only by 1% (30 microseconds divided by 3 milliseconds), so the effect of 50/60 Hz voltage noise is attenuated to one percent in this case.

Another bonus of self-capacitance measurements done in rapid sequence is the ability to accommodate motion altering capacitances C10 and C20 from one self-capacitance measurement to the next, so the longer the delay the less they cancel out. Short delays between measurements are thus important for reducing the effects of motion as well.

Incidentally, it might be of advantage to detect noise voltage sources (instead of rejecting them) in a different mode of operation not according to the invention, but the same circuitry. This can for example be done by measuring a row's or column's self-capacitance twice at an interval of optimally a half period at the frequency of interest, say 8 to 10 ms for 50/60 Hz and subtracting one measurement from the other, so that self-capacitances cancel but signals coupled from both measures' opposed voltage variations add up. Location accuracy is limited to whole rows or columns as only variations of row or column self-capacitance can be reliably measured in such a case, not variations of row-to-column cross-capacitance. Location accuracy can be improved, though, by checking which columns and rows pick up the strongest difference signal, and/or by correlating with cross-capacitance data obtained in a mode of operation according to the invention.

FIG. 3 shows a row and column electrode on a substrate, for example a printed circuit, of an embodiment of the invention. For better viewing, the substrate 100, usually opaque, is shown as transparent. On one side of it are row electrodes 101 of constant width and on the other side column electrodes 102 of constant width. Electrodes 101 and 102 could have different shapes, for example be narrow near crossovers and wide in-between. This, as explained further below, improves detecting range, but for narrow row and column pitches, constant width electrodes minimize the detrimental effect of the substrate's two sides' superposition shift or misregistration.

The substrate should be thick enough to minimize row-to-column cross-capacitance, but not so thick as to increase row and column electrodes' self-capacitances C10 and C20 via the substrate's dielectric to grounded adjacent row and column electrodes to the point of exceeding the self-capacitance-to-digital converter's input range. As a remark, row and column electrodes 101 and 102 extend sufficiently far away from the crossovers to provide reasonably uniform electric field conditions for each and every crossover. They extend a bit farther out where they are connected to connecting lines 201 and 202 in order to minimize the line's unwanted contribution to sensing. For the same reason, connecting lines 201 and 202 should be as thin as possible. As a remark, only the end of connecting lines 201, 202, are shown in FIG. 3, that is, where they contact electrodes 101, 102.

Figure 4:
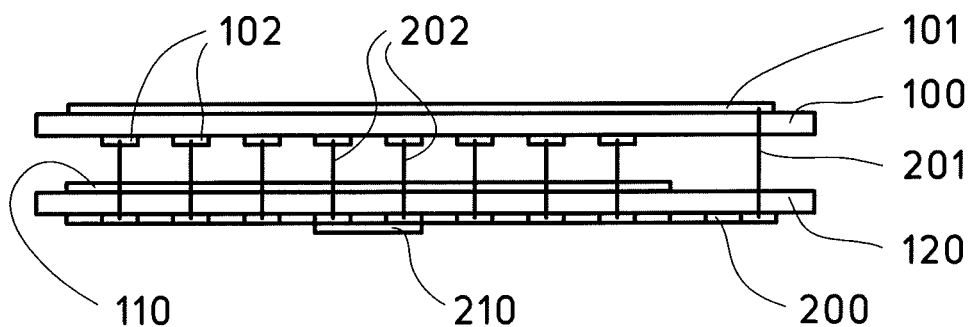
FIG. 4 is a view of an embodiment of the invention.

FIG. 4 shows an embodiment of the invention, comprising substrate 100 with row electrodes 101 on one side and column electrodes 102 on the other, and a second substrate 120 substantially parallel to substrate 100. Substrate 120 has a screen 110 on the side facing substrate 100 and measuring circuit 200 with self-capacitance-to-digital converter 210 on the side facing away from circuit 100. Connecting lines 201 (only the closest line is seen as the rest are hidden behind it) connect row electrodes 101 (only the closest one is seen, too) to circuit 200, and connecting lines 202 connect row electrodes 102 to measuring circuit 200. Only parts necessary to explain the embodiment's operation are shown in FIG. 4: for instance, mechanical means for holding circuits 100 and 120 together are not shown.

As the row and column electrode substrate 100 is inherently sensitive to dielectric features on either side of it, the side away from the dielectric or conducting features should face a dielectrically empty or at least a homogeneous space. This is unpractical as even distant objects may still interfere. Screen 110 remedies to this by shielding substrate 100 from external objects and circuitry, particularly measuring circuit 200 and part of connecting wires 201 and 202. Screen 110 should cover the array with a minimum of overlap to provide uniform electric field conditions on all crossover capacitances.

Some or all of the electrical/electronic circuitry can also be implemented on the array's substrate to minimize parasitic capacitances. Of course, unintended coupling between the circuitry and the array's row and column electrodes should be kept as low as possible by keeping them sufficiently apart and/or by shielding them from each other.

In order to save costs and reduce size of an embodiment having its circuitry implemented on one substrate, screen 110 may be integrated on substrate 100, on its side facing away from the dielectric or conducting features, at the cost of increased row and column electrodes' self-capacitances.

The shape of row and column electrodes also contributes to the quality of detection: constant width electrodes primarily detect dielectric inhomogeneities near their crossovers, where most of the cross-capacitance is concentrated. The weaker signals from remote features are thus harder to detect. This is a main concern in hidden object imaging, particularly for wall scanners or stud sensors, in which remote features like pipes, studs or electrical wiring rather than wall surface roughness or minute dielectric inhomogeneities should be detected.

Figure 5:
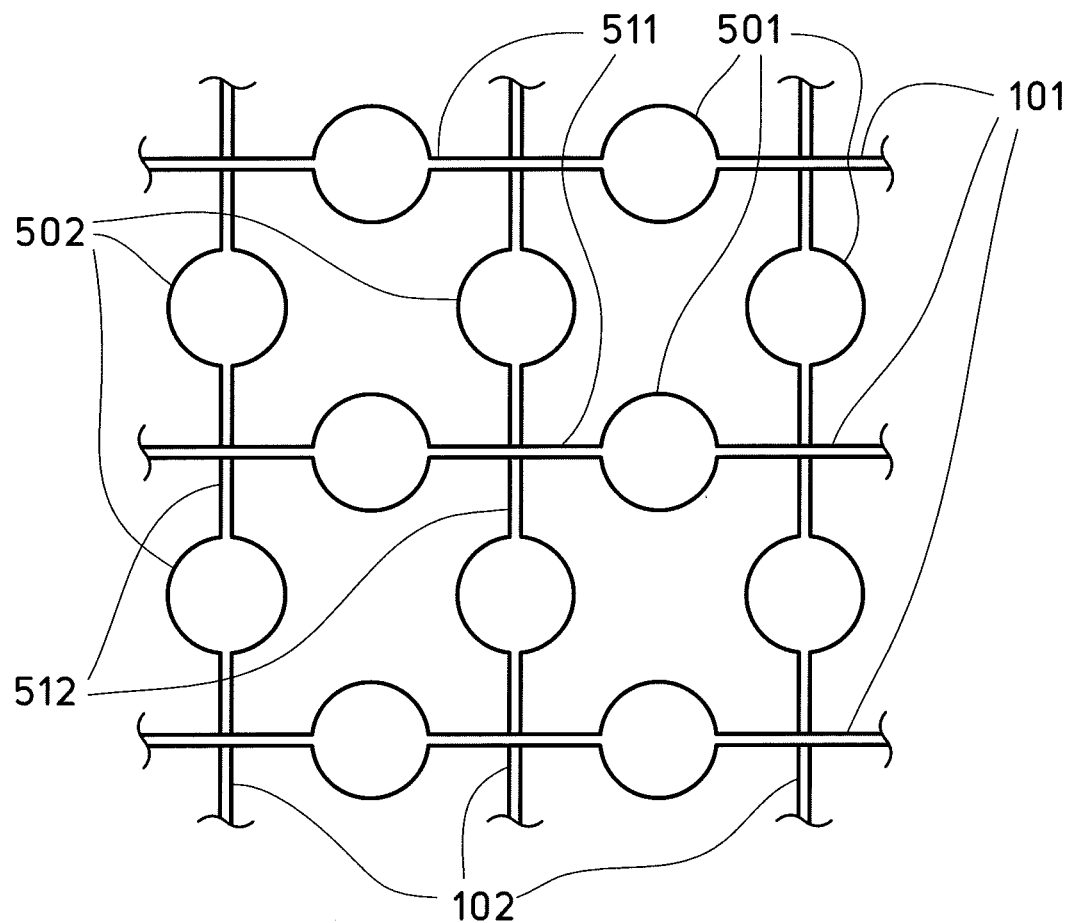
FIG. 5 is a partial view of shaped row and column electrodes, with row electrodes on one side of the substrate and column electrodes on the other.

FIG. 5 shows part of an array with rows and columns shaped for easier detection of remote objects. Its rows 101 consist of areas 501 connected by narrow conductors 511, and its columns 102 consist of series of areas 502 connected by narrow conductors 512. Areas 501, 502 are preferably round as depicted, or rhomboidal (diamond-shaped), but may have any other suitable shape. Areas 501, 502 may optimally be on one side of their substrate or for easier routing on both sides of it as shown in FIG. 5, with rows 101 on one side of a sufficiently thin substrate, and columns 102 on the other, strongly reducing the number of plated-through holes needed.

The improvement in remote feature detection lies in the strongly reduced mutual capacitance between rows 101 and columns 102, especially in the immediate vicinity of the crossovers. This results in reduced sensitivity to inhomogeneities nearest crossovers, while sensitivity to remote features remains about the same as for constant width electrodes.

Remote features are thus easier to detect, and the reduced sensitivity to dielectrics near the electrodes decreases the effect of a varying gap on mutual capacitance measurements. For instance, most stud sensors need to be re-calibrated on a dielectrically homogeneous area of the wall to be examined, with the risk of re-calibrating by mistake on an inhomogeneous area including a stud, for example. The shaped array's reduced sensitivity to gap and to the wall's average dielectric constant makes the need for re-calibrations less frequent or even unnecessary. And in many cases, a simple constant shift of all current calibration offsets may advantageously replace re-calibration.

FIGS. 6A and 6B are top and elevation views of a preferred device embodying the invention, a hand-held wall hidden object detector such as a stud sensor. FIG. 6A shows the embodiment 400 touching the wall 600 with spacers 405, preferably rollers. Its side facing wall 600 has a row and column electrode substrate 100. FIG. 6B shows the front face of embodiment 400, located in a plane substantially parallel to substrate 100, and including a display 410.

Device 400 may integrate the embodiment shown in FIG. 4, or any other suitable embodiment, with display 410 added. As dielectric features as displayed might not correspond exactly to actual hidden features, viewing should be as intuitive as possible. This can be helped by a display having about the same size as the extent of the row and column crossover area of substrate 100, and covering it at a reasonably short distance, thus providing the operator with the illusion of a window looking into the wall, especially if device 400 is moved along it. This makes it easier for an operator to identify hidden features, even with a low resolution display.

Another device embodying the invention has means for transmitting data to an external display, typically a smart phone or tablet computer instead of a display, which would significantly reduce its cost. The illusion of a window may still be created by adding a possibility to dock the smart phone or tablet computer on the device.

Capacitive imaging devices according to the invention are optimal for the applications above, as well as for multi-touch sensors and track pads. However, they may also be suitable in less obvious applications, like fingerprint sensing or mine detecting.

Arrays of row electrodes and column electrodes can have other shapes suitable for the application, for example concentric rows and radial columns, or parallels and meridians on a spherical surface. Rows and columns on a cylindrical surface can detect liquids in syringes and pumps.

The invention claimed is:

1. A method of measuring crossover capacitances of row and column electrodes in a capacitive imaging device including a plurality of spaced apart, side-by-side co-planar row electrode and a plurality of spaced apart, side-by-side co-planar column electrodes, wherein the row electrodes are transverse to and spaced apart from the column electrodes so that the row electrodes overlie the row electrodes at respective crossovers, each row electrode and each column electrode has a respective self-capacitance, and each crossover has a respective crossover capacitance, the method comprising the steps of:

grounding the column electrode having a first crossover with a row electrode, electrically connecting the row electrode of the first crossover to a capacitance-to-digital converter of a measuring circuit, and measuring a first capacitance that is a sum of the self-capacitance of the row electrode and the crossover capacitance of the first crossover, grounding the row electrode of the first crossover, electrically connecting the column electrode of the first crossover to the capacitance-to-digital converter of the measuring circuit, and measuring a second capacitance that is a sum of the self-capacitance of the column electrode and the crossover capacitance of the first crossover, electrically connecting the row electrode and the column electrode of the first crossover to the capacitance-to-digital converter of the measuring circuit and measuring a third capacitance that is a sum of the self-capacitances of the row and the column electrodes of the first crossover, and determining the crossover capacitance of the first crossover from the first, second, and third capacitances that have been measured.

2. The method of claim 1 including repeating the steps of claim 1 and measuring crossover capacitances of each of a plurality of crossovers of the row and column electrodes.

3. The method of claim 1 including, while measuring the first, second, and third capacitances, grounding all of the row and column electrodes other than the row electrode and the column electrode of the first crossover that are not grounded measuring the first, second, and third capacitances.

4. A method of measuring crossover capacitances of row and column electrodes in a capacitive imaging device including a plurality of spaced apart, side-by-side co-planar row electrode and a plurality of spaced apart, side-by-side co-planar column electrodes, wherein the row electrodes are transverse to and spaced apart from the column electrodes so that the row electrodes overlie the row electrodes at respective crossovers, each row electrode and each column electrode has a respective self-capacitance, and each crossover has a respective crossover capacitance, the method comprising:

electrically connecting together at least first and second of the row electrodes and electrically connecting together at least first and second of the column electrodes, wherein the first and second row electrodes and the first and second column electrodes overlie each other at first and second crossovers, grounding the first and second column electrodes, electrically connecting the first and second row electrodes to a capacitance-to-digital converter of a measuring circuit, and measuring a first capacitance that is a sum of the self-capacitances of the first and second row electrodes and the crossover capacitances of the first and second crossovers, grounding the first and second row electrodes, electrically connecting the first and second column electrodes to the capacitance-to-digital converter of the measuring circuit, and measuring a second capacitance that is a sum of the self-capacitances of first and second column electrodes and the first and second crossover capacitance of the first and second crossovers, electrically connecting the first and second row electrodes and the first and second column electrodes to the capacitance-to-digital converter of the measuring circuit and measuring a third capacitance that is a sum of the self-capacitances of the first and second row and first and second column electrodes of the first and second crossovers, and determining the crossover capacitance of the first and second crossovers from the first, second, and third capacitances that have been measured.

5. The method of claim 4 including, while measuring the first, second, and third capacitances, grounding all of the row and column electrodes, other than the first and second row electrodes and the first and second column electrodes which are not grounded in measuring the first, second, and third capacitances.

* * * * *